(12) United States Patent
Merrill, Jr. et al.

(10) Patent No.: US 6,552,025 B1
(45) Date of Patent: Apr. 22, 2003

(54) DIIMINO-PIPERAZINE DERIVATIVES FOR USE AS MODULATORS OF CELL REGULATION

(75) Inventors: Alfred H. Merrill, Jr., Dunwoody, GA (US); Lisa Warden, Stroudsburg, PA (US); Dennis C. Liotta, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/715,483

(22) Filed: Nov. 17, 2000

Related U.S. Application Data

(60) Provisional application No. 60/167,323, filed on Nov. 24, 1999.

(51) Int. Cl.$^7$ .................. A61K 31/496; C07D 241/02; C07D 295/00
(52) U.S. Cl. ............... 514/255.01; 514/238.5; 514/227.5; 544/382; 544/398; 544/402; 544/407; 544/162; 544/59
(58) Field of Search ............ 514/255.01, 238.5, 514/227.5; 544/382, 398, 402, 407, 162, 59, 394

(56) References Cited

U.S. PATENT DOCUMENTS

| | | | | |
|---|---|---|---|---|
| 2,837,568 A | * | 6/1958 | Zimmermann et al. | 260/566 |
| 5,073,635 A | | 12/1991 | Bowman et al. | 544/401 |
| 5,250,528 A | | 10/1993 | Oku et al. | 544/252 |

FOREIGN PATENT DOCUMENTS

| | | | |
|---|---|---|---|
| DE | 41 27 026 A1 | | 2/1993 |
| DE | 4127026 | * | 2/1993 |
| WO | WO 95/03054 A1 | | 2/1995 |
| WO | WO 99/41266 A1 | | 8/1999 |
| WO | 0137836 | * | 5/2001 |

OTHER PUBLICATIONS

Ma J. et al., "Delivery of Cytotoxic Drugs from Carrier Cells to Tumour Cells by Apoptosis", *Apoptosis*, vol. 3, pp. 195–202, (1998).

Merrill A.H., et al., "Bioactive Properties of Sphingosine and Structurally Related Compounds", *Handbook of Lipid Research*, vol. 8: Lipid Second Messengers, Ed. R.M. Bell et al., pp. 205–237, 1996.

Merrilll, A.H., "Long Chain Fatty Acids and Other Lipid Second Messengers", *Polyunsaturated Fatty Acids in Human Nutrition*, vol. 28, pp. 41–52, 1992.

Merrill A.H. et al., "Sphingolipids—The Engimatic Lipid Class: Biochemistry, Physiology, and Pathophysiology", *Toxicology and Applied Pharmacology*, vol. 142, pp. 208–225, 1997.

Smith E.R. et al., "Changing J774A. 1 Cells to New Medium Perturbs Multiple Signaling Pathways, Including the Modulation of Protein Kinase C by Endogenous Sphingoid Bases", *Journal of Biol. Chemistry*, vol. 272, No. 9, pp–. 5640–5646, 1997.

Smith E.R, et al., "Differential Roles of de Novo Sphingolipid Biosynthesis and Turnover in the "Burst" of Free Sphingosine and Sphinganine, and Their 1–Phosphates and N–Acyl–Derivatives, That Occurs upon Changing the Medium of Cells in Culture", *Journal of Biol. Chemistry*, vol. 270, No. 32, pp. 18749–18756, 1995.

Vesper H., et al, "Sphingolipids in Food and the Emerging Importance of Sphingolipids to Nutrition", *Am. Soc. Nutrit. Sci.*, pp. 1239–1250, 1999.

Barot, N. R. et al. "Heterocyclic imines and Amines. Part XII. Imino–Derivatives of Piperazine", *J. Chem. Soc.*, (XP–002158065) pp. 1009–0014, 1972.

Barot, N. et al., "Heterocyclic Imines and Amines. Part XVI 2,6–Diaminopyrazine and its 1–Oxide from Iminodiacetonitrile", *J. Chem. Soc.*, (XP–002158066), pp. 606–612, 1973.

Elvidge, J.A., "Heterocyclic Imines and Amines. Part IX. Glutarmidine and the Imidine from α–Phenylglutaronitrile", *J. Chem Soc.*, (XP–002158067), pp. 208–215, 1959.

Ghosh, T.K. et al., "Intracellular Calcium Release Mediated by Sphingosine Derivatives Generated in Cells", *Science*, vol. 248, pp. 1653–1656, 1990 (XP 000647701).

Warden, L. A., et al., "Identification of Ammonium Ion and 2,6–Bis (w–aminobutyl)–3,5–diiminopiperazine as Endogenous Factors that Account for the "Burst" of Sphinogosine upon Changing the Medium of J774 Cells in Culture", *J. Biol. Chem.*, vol. 274, No. 48, pp. 33875–33880, 1999 (XP–002158064).

* cited by examiner

*Primary Examiner*—Richard L. Raymond
*Assistant Examiner*—Sudhaker B. Patel
(74) *Attorney, Agent, or Firm*—Kilpatrick Stockton LLP

(57) ABSTRACT

Compositions, methods of use, isolation and biosynthesis of diimino-piperazine derivatives useful for the modification of sphingolipid metabolism and other biological functions are described. The preferred derivative is 2,6-bis-(ω-aminobutyl)-3,5-diimino-piperazine. This is a naturally occurring biochemical compound isolated from cells. The diimino-piperazine derivatives are useful as therapeutic agents when administered to patients to treat diseases and disorders involving cell regulation.

11 Claims, 9 Drawing Sheets

DIIMINO-PIPERAZINE DERIVATIVES FOR USE AS MODULATORS OF CELL REGULATION

This application claims priority to U.S. Provisional Patent Application No. 60/167,323, filed Nov. 24, 1999.

The U.S. Government has rights in this invention arising out of NIH grant GM46368 and funding from the Office of Naval Research.

FIELD OF THE INVENTION

The present invention relates to diiminopiperazine derivatives and the use of these bioactive compounds in altering the metabolism and functions of sphingolipids, glycerolipids, and other biochemicals to affect diverse cell behaviors, including signal transduction, cell growth and survival.

BACKGROUND OF THE INVENTION

Sphingolipids are a group of lipids found in all eukaryotic cells as well as some prokaryotes and viruses. Sphingosine and other long-chain (sphingoid) bases are the structural backbones of sphingolipids and have been found to affect diverse cellular systems when added to in vitro assays, cells, and in vivo when applied to skin, injected or fed in the diet. These affected systems include, but are not limited to, protein kinase C, $Na^+$, $K^+$-ATPase, phosphatidic acid phosphatase, phopholipases (including phospholipase D), retinoblastoma protein phosphorylation, and sphingosine-activated protein kinases. The inhibition of protein kinase C has been studied most thoroughly in vitro using mixed micellar assays of the purified enzyme as well as by evaluation of cellular functions dependent on this enzyme in platelets, neutrophils, HL-60 cells, and many other systems. Sphingosine inhibits protein kinase C by acting as a competitive inhibitor of activation by diacylglycerol, phorbol dibutyrate, and, for some isozymes, calcium, and also blocks activation by unsaturated fatty acids and other lipids. The exact mechanism by which sphingoid bases inhibit protein kinase C remains unknown. However, since protein kinase C binds to membranes through interactions with diacylglycerol and negatively charged phophatidylserine, sphingosine may be localized in regions of acidic lipids and block enzyme binding or activity. Modified forms of sphingosine (such as sphingosine 1-phosphate and N-acylsphingosines, or ceramides) are also biologically active.

Free sphingoid bases (sphinganine and sphingosine), sphingosine-1-phosphate, and ceramides are formed endogenously as lipid mediators. Sphingolipids have been studied as intracellular lipid messengers for agonists such as tumor necrosis factor, interleukin-1β, platelet-derived growth factor, nerve growth factor, cytotoxic agents, and are involved in various forms of stress.

The changing of cells in culture to fresh medium has been found to induce a transient "burst" of sphingosine, sphinganine, and other bioactive lipids to levels that are sufficient to affect at least one signaling pathway, the membrane association and activity of protein kinase C. This increase in free sphinganine, as well as sphinganine-1-phosphate and dihydroceramide, upon the addition of new medium arises from de novo sphingolipid biosynthesis. In contrast, the increase in sphingosine (and sphingosine-1-phosphate and ceramide) arises mainly from the turnover of complex sphingolipids.

Because these sphingolipid metabolites are highly active and control important cell functions, which include, but are not limited to, inflammation, growth, cell differentiation and development, cell death, and aging, there is a need for methods and compositions for controlling or modulating sphingolipid metabolism. These methods and compositions will be useful in controlling the biological processes affected by sphingolipids and for the treatment of diseases that have disorders involving cell regulatory pathways. Furthermore, studies have also shown that other bioactive lipid metabolites change during the sphingosine "burst" (such as diacylglycerols), hence, agents that affect one cell signaling pathway may have important effects on other cell signaling systems, and have broad pharmacologic utility. In addition to the implications of these compounds for health, the ability to modulate cell behavior can have applications in industry for the production of biomolecules using cells in culture and other types of bioreactors.

SUMMARY OF THE INVENTION

Diimino-piperazine derivatives and their use as modulators of cell regulation are provided. These compounds are particularly useful for the inhibition of sphingolipid metabolism as evidenced by their ability to suppress the sphingosine "burst" that occurs when cells in culture are changed to new medium.

In a first preferred embodiment, the derivatives, including all stereo-, regio- and geometric isomers, have the following structural formula:

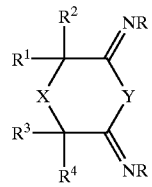

wherein

R is independently H, alkyl, aryl, heteroaryl, —C(O)R, —C(NR)OR, —C(O)$NR_2$, —C(NR)$NR_2$, —C(NR)SR or —C(S)$NR_2$;

$R^1$, $R^2$, $R^3$ and $R^4$ are independently H, R, $(CH_2)_n OR$, $(CH_2)_n NR_2$, $CH_2 O(CH_2)_n OR$, or $CH_2 O(CH_2)_n NR_2$ where n=1 to 6; and X and Y are independently O, $NR^1$, S or $CR^1_2$.

In a second preferred embodiment, the derivatives, including all stereo-, regio- and geometric isomers, have the following structural formula:

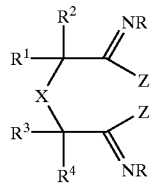

wherein

R is independently H, alkyl, aryl, heteroaryl, —C(O)R, —C(NR)OR, —C(O)$NR_2$, —C(NR)$NR_2$, —C(NR)SR or —C(S)$NR_2$;

$R_1$, $R_2$, $R^3$ and $R^4$ are independently H, R, $(CH_2)_n OR$, $(CH_2)_n NR_2$, $CH_2 O(CH_2)_n OR$, or $CH_2 O(CH_2)_n NR_2$ where n=1 to 6;

X is independently O, $NR^1$, S or $CR^1_2$; and

Z is independently $OR^1$, $NR^1_2$, $SR^1$.

In a third preferred embodiment, the derivatives, including all stereo-, regio- and geometric isomers, have the following structural formula:

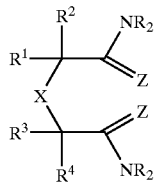

wherein
R is independently H, alkyl, aryl, heteroaryl, —C(O)R, —C(NR)OR, —C(O)NR$_2$, —C(NR)NR$_2$, —C(NR)SR or —C(S)NR$_2$;
R$^1$, R$^2$, R$^3$ and R$^4$ are independently H, R, (CH$_2$)$_n$OR, (CH$_2$)$_n$NR$_2$, CH$_2$O(CH$_2$)$_n$OR, or CH$_2$O(CH$_2$)$_n$NR$_2$ where n=1 to 6;
X is independently O, NR$^1$, S or CR$^1{}_2$; and
Z is independently O, NR$^1$ or S.

In a fourth preferred embodiment, the derivatives, including all stereo-, regio- and geometric isomers, have the following structural formula:

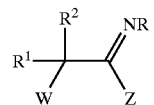

wherein
R is independently H, alkyl, aryl, heteroaryl, —C(O)R, —C(NR)OR, —C(O)NR$_2$, —C(NR)NR$_2$, —C(NR)SR or —C(S)NR$_2$;
R$^1$, R$^2$, R$^3$ and R$^4$ are independently H, R, (CH$_2$)$_n$OR, (CH$_2$)$_n$NR$_2$, CH$_2$O(CH$_2$)$_n$OR, or CH$_2$O(CH$_2$)$_n$NR$_2$ where n=1 to 6;
W is independently OR$^1$, NR$^1{}_2$, SR$^1$, (CH$_2$)$_n$OR$^1$, (CH$_2$)$_n$SR$^1$ or (CH$_2$)$_n$NR$^1{}_2$ where n=1 to 6;
Z is independently OR$^1$, NR$^1{}_2$, SR$^1$.

The most preferred diimino-piperazine derivative has the following chemical structure:

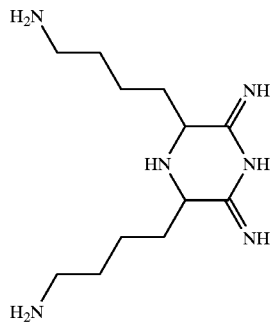

The chemical name of the most preferred compound is 2,6-bis-(ω-aminobutyl)-3,5-diimino-piperazine. This is a naturally occurring biochemical compound isolated from cells, particularly macrophages.

The derivatives can be synthesized using a series of reactions known to those skilled in the art, one example of which proceeds through a monomeric intermediate that is allowed to undergo a series of alkylation and subsequent deprotection reactions described in more detail below.

The diimino-piperazine derivatives alter sphingolipid metabolism as well as the metabolism of other bioactive mediators such as diacylglycerols, and are therefore useful when administered to patients with abnormalities that can be modified to achieve health benefit. Diseases that are in this category include, but are not limited to, inflammatory diseases, cancer, heart attack, strokes and other cardiovascular disease, AIDS, and neuronal and neuromuscular disease such as Alzheimer's Disease and Parkinson's Disease.

It is therefore an object of the present invention to provide a new category of bioactive compounds, namely diimino-piperazine derivatives, as naturally occurring or synthetic modulators of cell regulation.

It is a further object of the present invention to provide a treatment for diseases such as cancer that respond to modulation of cell regulation by administration of these compounds to patients.

BRIEF DESCRIPTION OF THE DRAWINGS

FIG. 8B shows the elution of the suppressive activity upon chromatography of the pooled 0.5 M NaCl eluate from the column in FIG. 8A (after concentration by lyophilization) on a 2×60 cm Bio-Rad P2 column (the volume of each fraction was 3 ml).

DETAILED DESCRIPTION OF THE INVENTION

Figure 1:
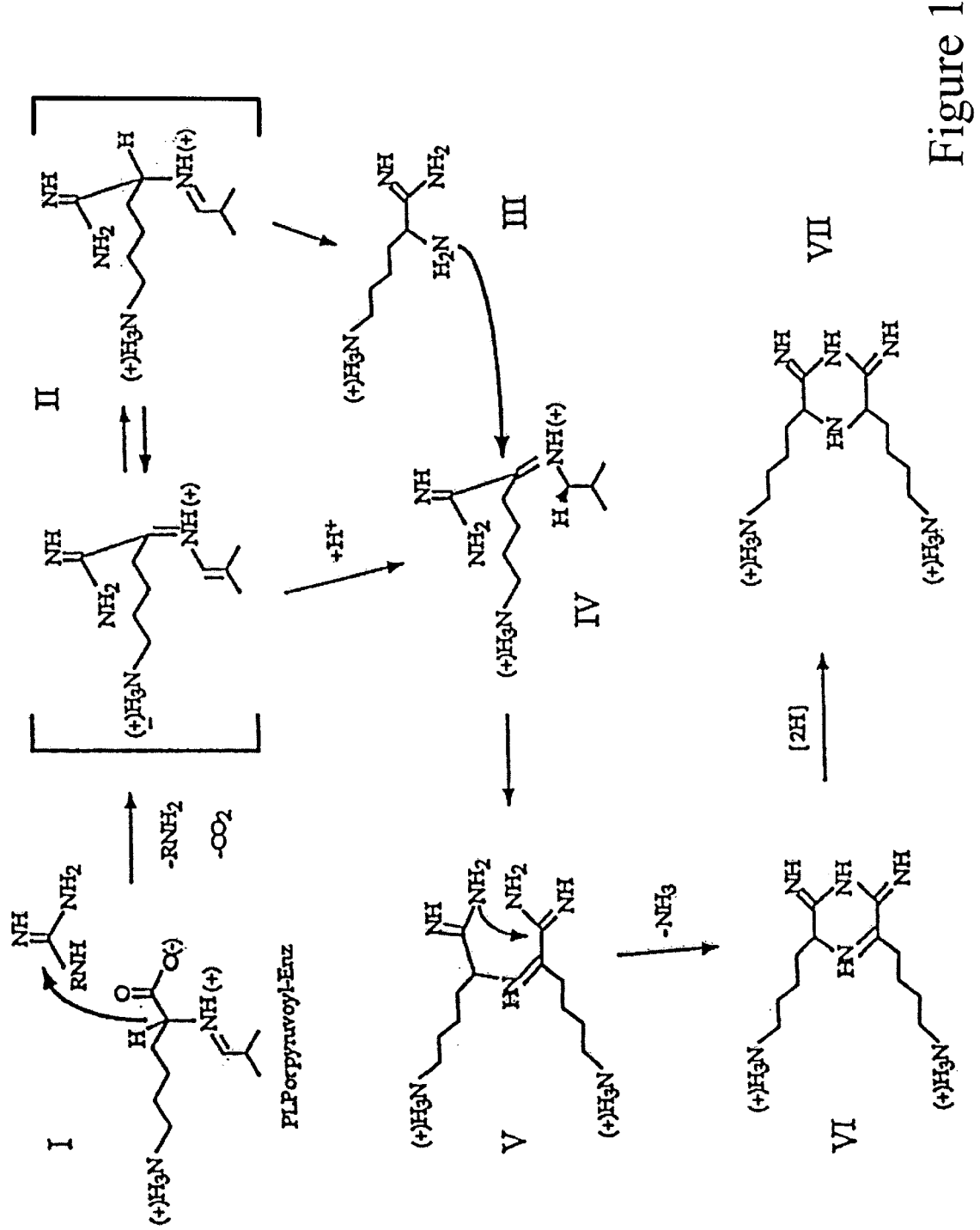
FIG. 1 is a flow diagram showing a scheme for a biomimetic synthesis of the diimino-piperazine derivatives described herein.

Diimino-piperazine derivatives are described herein that alter sphingolipid metabolism and other aspects of cell regulation. The derivatives are useful as pharmacologic agents when administered to patients for the treatment of disorders or diseases involving cell signaling pathways.

The derivatives are low molecular weight, cationic compounds purified or isolated from biological samples, such cell culture, using biochemical purification methods known to those skilled in the art and described in more detail below. Alternatively, the derivatives are chemically synthesized using a series of reactions known to those skilled in the art and described below. The derivatives are characterized by their ability to inhibit sphingolipid metabolism, particularly sphingosine "burst".

Definitions

As used herein, the term "isolated enantiomer" refers to a nucleoside composition that includes at least approximately 95% to 100%, or more preferably, over 97% of a single enantiomer of that nucleoside.

The term alkyl, as used herein, unless otherwise specified, refers to a saturated straight, branched, or cyclic, primary, secondary, or tertiary hydrocarbon, typically of $C_1$ to $C_{18}$ and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl and 2,3-dimethylbutyl. The alkyl group can be optionally substituted with one or more moieties selected from the group consisting of hydroxyl, carboxylic acid or ester, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. Suitable protecting groups are described, for example, in Greene, et al., "Protective Groups in Organic Synthesis," John Wiley and Sons, Second Edition, 1991, hereby incorporated by reference.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent. The term aralkyl or arylalkyl refers to an aryl group with an alkyl substituent. The term halo, as used herein, includes chloro, bromo, iodo and fluoro.

The term acyl refers to moiety of the formula —C(O)R', wherein R' is alkyl; aryl, alkaryl, aralkyl, heteroaromatic, heterocyclic, alkoxyalkyl including methoxymethyl; aryla-lkyl including benzyl; aryloxyalkyl, such as phenoxymethyl; aryl including phenyl optionally substituted with halogen, $C_1$ to $C_4$ alkyl or $C_1$ to $C_4$ alkoxy or the residue of an amino acid.

As used herein, a leaving group means a functional group that is cleaved from the molecule to which it is attached under appropriate conditions.

The term heteroaryl or heterocyclic, as used herein, refers to a cyclic moiety that includes at least one sulfur, oxygen, or nitrogen in the ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2, 4thiadiazolyl, isoxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heterocyclic base can be protected as necessary or desired. Suitable protecting groups are well known to those skilled in the art, and include, but are not limited to, trimethylsilyl, triethylsilyl, dimethylhexylsilyl, t-butyldimethylsilyl, t-butyldiphenylsilyl and triisopropylsilyl. The alkyl group can be optionally substituted with one or more moieties selected from the group consisting of hydroxyl, carboxylic acid or ester, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term alkylheteroaryl refers to an alkyl group substituted by a heteroaryl substituent.

Diimino-piperazine Derivative Chemical Structures

In a first preferred embodiment, the derivatives, including all stereo-, regio- and geometric isomers, have the following structural formula:

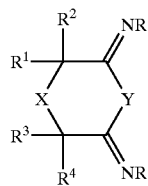

wherein

R is independently H, alkyl, aryl, heteroaryl, —C(O)R, —C(NR)OR, —C(O)NR$_2$, —C(NR)NR$_2$, —C(NR)SR or —C(S)NR$_2$;

R$^1$, R$^2$, R$^3$ and R$^4$ are independently H, R, (CH$_2$)$_n$OR, (CH$_2$)$_n$NR$_2$, CH$_2$O(CH$_2$)$_n$OR, or CH$_2$O(CH$_2$)$_n$NR$_2$ where n=1 to 6; and X and Y are independently O, NR$^1$, S or CR$^1{}_2$.

In a second preferred embodiment, the derivatives, including all stereo-, regio- and geometric isomers, have the following structural formula:

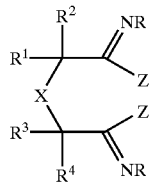

wherein

R is independently H, alkyl, aryl, heteroaryl, —C(O)R, —C(NR)OR, —C(O)NR$_2$, —C(NR)NR$_2$, —C(NR)SR or —C(S)NR$_2$;

R$^1$, R$^2$, R$^3$ and R$^4$ are independently H, R, (CH$_2$)$_n$OR, (CH$_2$)$_n$NR$_2$, CH$_2$O(CH$_2$)$_n$OR, or CH$_2$O(CH$_2$)$_n$NR$_2$ where n=1 to 6;

X is independently O, NR$^1$, S or CR$^1{}_2$; and

Z is independently OR$^1$, NR$^1{}_2$, SR$^1$.

In a third preferred embodiment, the derivatives, including all stereo-, regio- and geometric isomers, have the following structural formula:

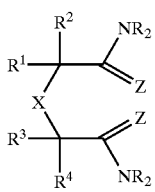

wherein

R is independently H, alkyl, aryl, heteroaryl, —C(O)R, —C(NR)OR, —C(O)NR$_2$, —C(NR)NR$_2$, —C(NR)SR or —C(S)NR$_2$;

R$^1$, R$^2$, R$^3$ and R$^4$ are independently H, R, (CH$_2$)$_n$OR, (CH$_2$)$_n$NR$_2$, CH$_2$O(CH$_2$)$_n$OR, or CH$_2$O(CH$_2$)$_n$NR$_2$ where n=1 to 6;

X is independently O, NR$^1$, S or CR$^1{}_2$; and

Z is independently O, NR$^1$ or S.

In a fourth preferred embodiment, the derivatives, including all stereo-, regio- and geometric isomers, have the following structural formula:

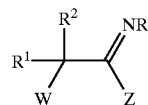

wherein

R is independently H, alkyl, aryl, heteroaryl, —C(O)R, —C(NR)OR, —C(O)NR$_2$, —C(NR)NR$_2$, —C(NR)SR or —C(S)NR$_2$;

R$^1$, R$^2$, R$^3$ and R$^4$ are independently H, R, (CH$_2$)$_n$OR, (CH$_2$)$_n$NR$_2$, CH$_2$O(CH$_2$)$_n$OR, or CH$_2$O(CH$_2$)$_n$NR$_2$ where n=1 to 6;

W is independently OR$^1$, NR$^1{}_2$, SR$^1$, (CH$_2$)$_n$OR$^1$, (CH$_2$)$_n$SR$^1$ or (CH$_2$)$_n$NR$^1{}_2$ where n=1 to 6;

Z is independently OR$^1$, NR$^1{}_2$, SR$^1$.

The most preferred diimino-piperazine derivative has the following chemical structure:

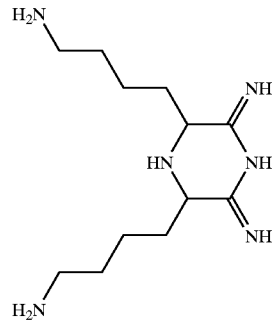

The chemical name of the most preferred compound is 2,6-bis-(ω-aminobutyl)-3,5-diimino-piperazine. Based on its frog-like appearance, this compound has been given the name "batrachamine" after the Greek word "batracheios" meaning of or belonging to a frog. This compound is a naturally occurring, low molecular weight, cationic compound isolated from cells in culture, particularly macrophages, as described in more detail below in the examples. The compound is also synthesized using chemical synthesis reactions as described in more detail in the following section.

Methods of Producing Diimino-piperazine Derivatives

The diimino-piperazine derivative compounds, particularly 2,6-bis-(ω-aminobutyl)-3,5-diimino-piperazine, are low molecular weight, cationic compounds purified or isolated from biological samples such as cells or cell lines using standard biochemical purification techniques well know to those skilled in the art. The preferred molecular weight of the derivative is less than 3000 daltons. More preferably, the molecular weight of the derivative is less than 250 daltons. Most preferably the molecular weight is between 130 and 240 daltons. Exemplary cell lines from which the derivatives are isolated or purified include J774 cells, Swiss 3T3 cells, NIH-3T3 cells, A431 cells, NG108-15 cells, and primary cultures of rat hepatocytes and mouse peritoneal macrophages. The preferred cell line from which the diimino-piperazine derivative is isolated is the murine macrophage J774 cell line. A detailed description of the isolation and characterization of 2,6-bis-(w-aminobutyl)-3,5-diimino-piperazine is described below in the examples.

The diimino-piperazine derivatives described herein are believed to be naturally biosynthesized using a series of reactions known to those skilled in the art that proceed through a monomeric intermediate (diaminohexanamidine) that undergoes condensation and cyclization by reactions such as those proposed (and indicated by Roman numerals) in FIG. 1. The decarboxylation of amino acids is a common reaction catalyzed by enzymes with reactive aldehyde moieties in the active site (pyridoxal 5'-phosphate or pyruvoyl groups), and the intermediate is utilized to form carbon-carbon bonds with a co-substrate with a suitable leaving group (for example, in the reactions catalyzed by δ-aminolevulinate synthase and serine palmitoyltransferase). With a guanidinium compound (e.g., arginine) as the co-substrate, this reaction produces the amidino moiety of batrachamine by reactions I and II. As is also shown in FIG. 1, pyridoxal 5'-phosphate- (and pyruvoyl-) enzymes are known to effect transformations that produce the types of amine and ketamine intermediates shown in II to IV. These may be used to condense (V) and cyclize (V to VI) to form the core batrachamine structure. Only one additional step (reduction) is needed to yield VII.

Figure 2:
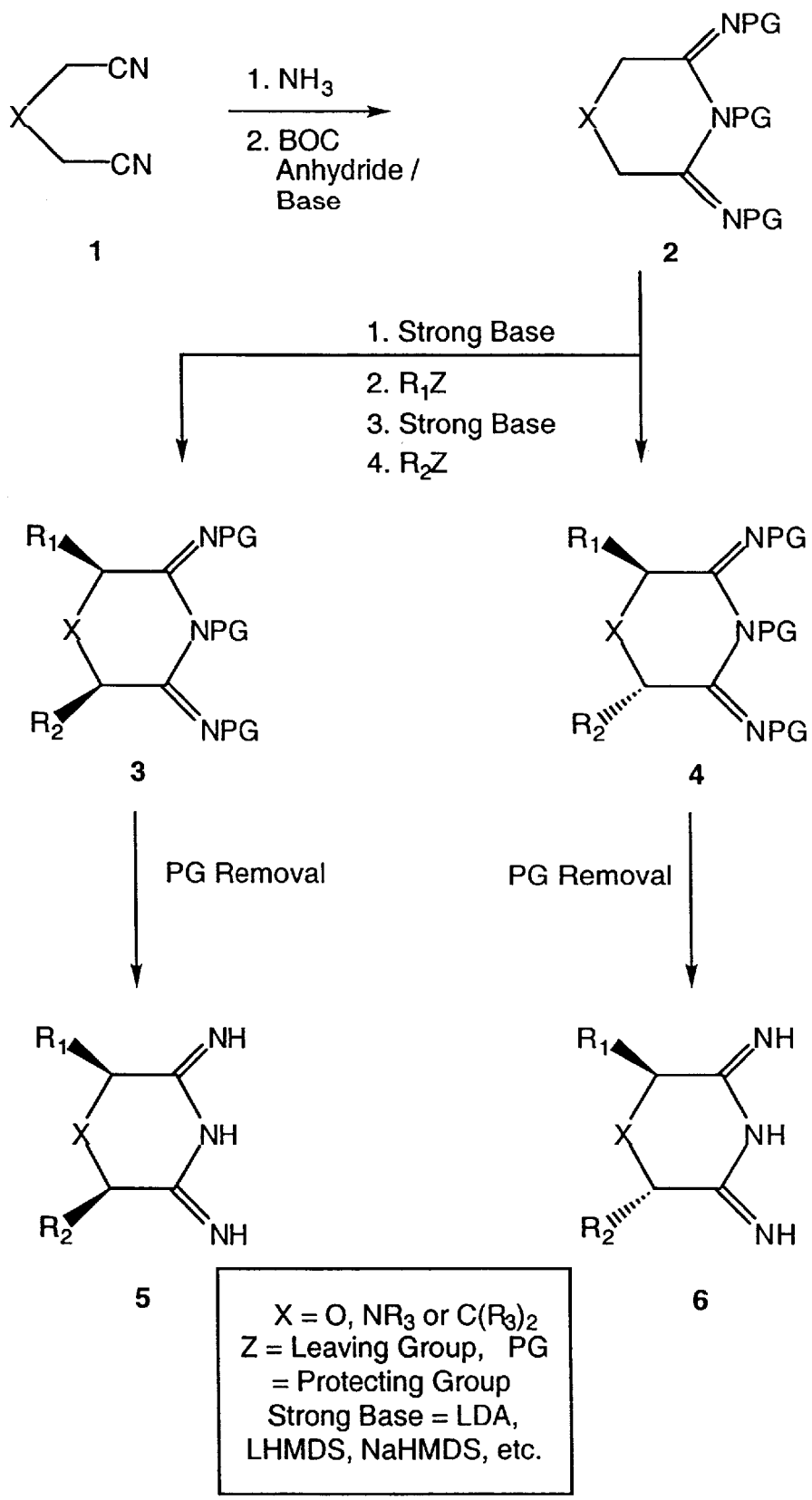
FIG. 2 is a flow diagram showing an alternative scheme for the synthesis of the diimino-piperazine derivatives described herein.

The diimino-piperazine derivatives can be synthesized using the following approaches shown schematically in FIG. 2. Bis-nitrile 1 is cyclized by exposure to ammonia or an ammonia surrogate (e.g., $HNTMS_2$, azide anion, —NHBOC anion, etc.). Replacement of any amino hydrogens with a suitable protecting group (e.g., t-BOC) produces the versatile intermediate2. Thus, sequential double alkylation, followed by deprotection, results in the formation of 5 and 6. As a consequence of $A_{1,2}$-strain, trans-isomer 6 is probably the major isomer produced in the alkylation process. For the cis-isomer, a variety of equilibration conditions well known to those skilled in the art will permit epimerization of 4 to 3 or 6 to 5. In addition, 6 can be prepared using a variety of enantioselective synthesis approaches well known to those skilled in the art (e.g., through the use of chiral auxiliaries, such as methyloxycarbonyl groups). If this is not effective, kinetic resolution approaches can be used (i.e., acylation of 6, followed by a protease-catalyzed hydrolysis).

Although not wishing to be bound by the following theory, it is believed that the mechanism for the suppression of the sphingosine burst by the diimino-piperazine derivativesis caused by the compounds acting as lysoosmotrophic factors. Alternatively, or additionally, the compounds may function as inhibitors of sphingolipid turnover by inhibiting enzymes that have an acidic pH optima.

Administration of Diimino-piperazine Derivatives

The diimino-piperazine derivatives described herein inhibit sphingolipid metabolism and are therefore useful when administered as a pharmacological composition to patients to treat diseases and disorders in which cell signaling pathways are concerned, such as cancer, AIDS, Alzheimer's Disease, Parkinson's Disease, heart attacks, strokes, inflammatory disease, immune disorders, radiation damage to normal tissue, sepsis, and the like. The derivatives may be combined with a pharmaceutically acceptable carrier or excipient as a pharmaceutical composition to facilitate administration.

The pharmaceutical compositions provided herein are intended for parenteral, topical, oral or local administration. Preferably, the pharmaceutical compositions are administered parenterally, e.g., intravenously, subcutaneously, intradermally, or intramuscularly. Thus, compositions are provided for parenteral administration that include a solution of the diimino-piperazine derivatives described above dissolved or suspended in an acceptable carrier, preferably an aqueous carrier. A variety of aqueous carriers may be used, such as, for example, water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the compounds are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, such as lecithin, for intranasal delivery.

The amount administered to the patient will vary depending upon what is being administered, the state of the patient and the manner of administration. In therapeutic applications, compositions are administered to a patient suffering from a disease or disorder involving cell signaling pathways in an amount sufficient to inhibit or at least partially arrest the symptoms of the disease or disorder and its complications. An amount adequate to accomplish this is defined as "therapeutically effective dose." Amounts effective for this use will depend on the severity of the disease, the particular composition, and the weight and general state of the patient. Generally, the dose will be in the range of about 1 mg to about 5 g per day, preferably about 100 mg per day, for a 70 kg patient.

The present invention is further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention or the scope of the appended claims.

EXAMPLE 1

Purification and Characterization of a Diiminopiperazine Derivative Having Sphingolipid Metabolism Inhibitory Activity Cell Culture Conditions J774A.1 cells (No. TIB 67, a murine macrophage-like transformed cell line) were obtained from the American Type Culture Collection (Rockville, Md.) and grown in DMEM and 10% FBS and sodium bicarbonate (3.7 g/l) in a spinner flask at 37° C. and an atmosphere of 5% $CO_2$. Cells were passaged every two to three days by a 1:4 dilution with fresh medium to a density of approximately $2.5 \times 10^5$ cells/ml. Cells were used between passages 3 and 24.

Analysis of the Sphingosine "Burst"

Unless indicated differently, suspended cells were removed from the spinner flask, collected by gentle centrifugation (in a table top centrifuge), resuspended in new medium, added to 60 mm tissue culture dishes at 5 to $7.5 \times 10^5$ cells per 2 ml of medium. Under these conditions, the cells adhere to the dish rather than grow in suspension. The cells were incubated at 37° C., 5% $CO_2$, for three days before beginning by removing the conditioned medium and adding fresh medium to initiate the "burst".

After incubation of the cells, the medium was removed, 0.5 ml of ice-cold methanol added, and the cells scraped from the dishes with a rubber spatula. The plates were scraped again with 0.4 ml of deionized water, followed by 0.4 ml of methanol. Cells and washes were pooled in 13×100 mm test tubes, 200 to 300 pmol of $C_{20}$-sphinganine added as an internal standard, and the long-chain bases extracted and analyzed by HPLC (as described by Merrill, A. H., Jr., et al., (1988) Anal. Biochem. 171, 373–381) with $C_{20}$-sphinganine as an internal standard.

Purification of the "Burst" Suppression Factors

Conditioned media were collected over time from the suspension cultures of the J774 cells and stored frozen at −20° C. until used. The following steps have proven to be optimal in the purification scheme: 1) The media are separated into high and low molecular weight species by ultrafiltration of 5L of conditioned media using an Amicon DC2™ filtration device with a Diaflo™ hollow fiber filtration cartridge (type HIP3-20-1806 with a molecular weight cut-off of 2000 to 3000 daltons) (W. R. Grace & Co. Beverly, Mass.). All of the suppressive activity was recovered in the ultrafiltrate. 2) The cationic species in the ultrafiltrate was isolated by ion exchange chromatography using a Bio-Rex 70™ macroreticular carboxylic acid cation exchange resin (Bio-Rad, Richmond, Calif.). Three liters of the ultrafiltrate was applied (at 4° C.) to a column (6×15 cm) containing approximately 100 grams of the pre-swollen, 100–200 wet mesh size resin. After applying the sample, the column was washed with 6 liters of ultra pure $H_2O$, followed by 0.5 liter of 0.1 M NaCl. The suppressive factor(s) were then step eluted with 0.5 liters of 0.5 M NaCl. 3) The 0.5 M NaCl eluate from the Bio-Rex 70™ column was concentrated to approximately 10 ml by lyophilization, then applied to a 2×60 cm P2 column (Bio-Rad Bio-Gel Polyacrylamide Gel, Fine, 100–200 mesh). The column was eluted with ultra pure $H_2O$ (sterilized) and 1 to 2 ml fractions were collected. The fractions containing suppressive activity were identified by bioassay with J774A.1 cells and stored at −20° C. in pooled fractions of 3 to 5 ml each (I to IV in FIG. 8).

Chemical Analysis and Structural Characterization

Thin-layer chromatography (TLC) was conducted using cellulose plates (Eastman Kodak Cellulose 13254) developed with butanol: acetic acid:water (15:5:3, v/v/v) and silica plates (EM DC Plastikfolkien Kiegelgel 60) developed with methanol. The amino compounds were detected with ninhydrin (sprayed on the plate as a 0.25% solution in acetone, air dried, and heated for two to three minutes) or ortho-phthalaldehyde (sprayed on the plate as a 0.20% solution in acetone).

Ammonium ion was analyzed by standard clinical chemistry techniques. The organic amine content is estimated using the TNBS (2,4,6 trinitrobenzene sulfonic acid) method (as described by Merrill, A. H., Jr., et al., (1988) Anal. Biochem. 171, 373–381). Since the molar extinction coefficient was not known, an average of the other amino acids in the foregoing reference was used (e 20,000 M−1 cm−1 at 420 nm).

$^1$H-NMR spectra were recorded on a Nicolet NT-360™ (361.03 MHz), a General Electric QE-300™ (300.15 MHz), or a General Electric GN-500™ (500.10 MHz) spectrometer; the following abbreviations are used; s: singlet; d: doublet; t: triplet; q: quartet; qn: quintet; m: multiplet; br: broad. The $^{13}$C-NMR spectra were recorded on a General Electric QE-300 (75.48 MHz) with $CDCl_3$ (triplet, d=77.00 ppm), $d_4$-methanol (septet, d=49.00 ppm), or $d_6$-DMSO (septet, d=39.50 ppm) as an internal standard. All $^{13}$C-NMR spectra were obtained using the attached proton test (APT, quaternary carbons only or quaternary and methylene phased up; methyl and methine phased down) pulse sequence. Infrared spectra were obtained using a Perkin-Elmer 1430 ratio recording spectrometer. Mass spectrometry was performed using a JEOL JMS-SX102/SX102A/E, five-sector, tandem (MS1-MS2-MS3) mass spectrometer (as described by Visek, W. J. (1978) Amer. J. Clin. Nutr. 31, S216–S220 and Khan, W. A., et al., (1991) Biochem. J. 278, 387–392). Full-scan negative ion fast atom bombardment (FAB) mass spectra was acquired using MS1 and frit-FAB in which the solvent was 2:1 $CHCl_3$/MeOH containing 1% triethanolamine.

The Sphingosine "Burst" of J774 A.1 Cells

Figure 3:
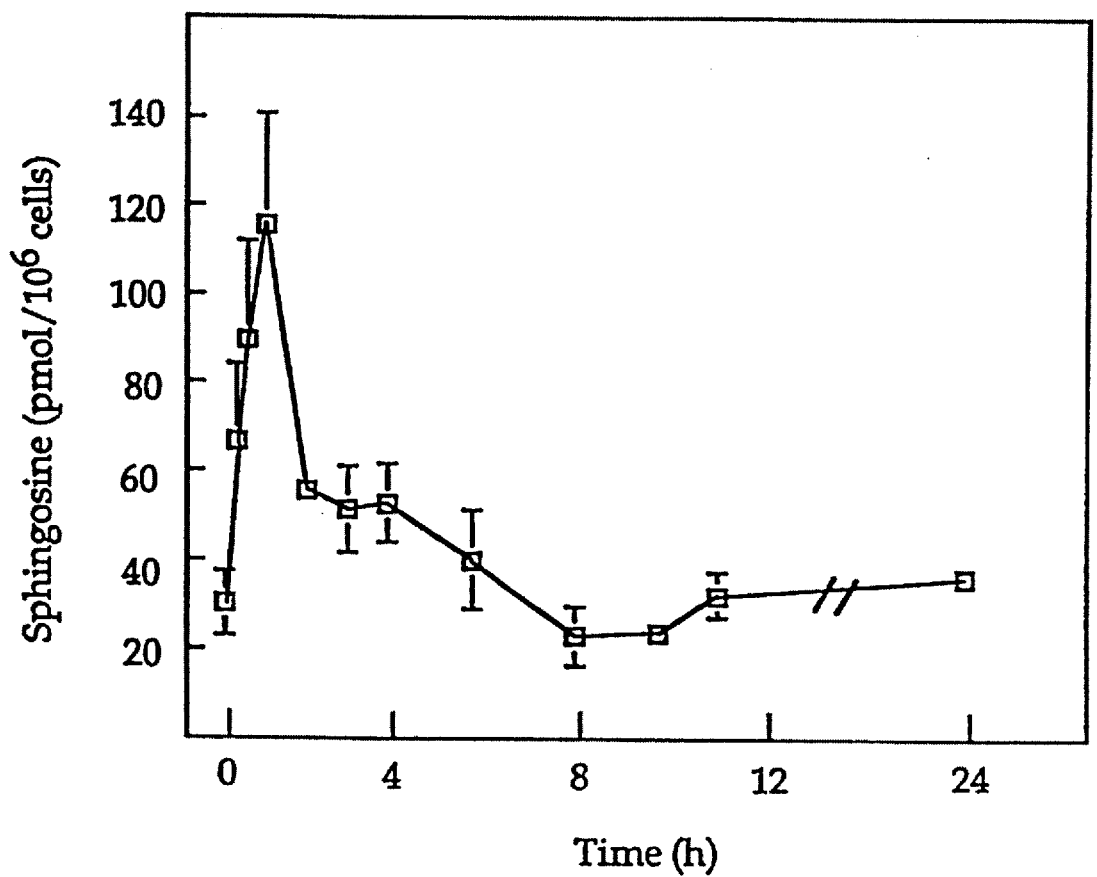
FIG. 3 is a graph showing free sphingosine mass after removal of conditioned culture medium. J774 cells were cultured for 3 days, then the conditioned culture medium was removed and replaced with fresh medium (DMEM without FBS) for various times. Results are the mean±SD (pmol/10$^6$ cells) from triplicate samples of a representative experiment.

Shown in FIG. 3 is a typical response of J774 A.1 cells upon changing from old to new medium. There was an increase in sphingosine to greater than 100 pmol per $10^6$ cells within an hour (which is termed the sphingosine burst) followed by a return to a basal level (ca 20 pmol) in approximately 8 hours.

Reversibility of the Sphingosine Burst

Figure 4:
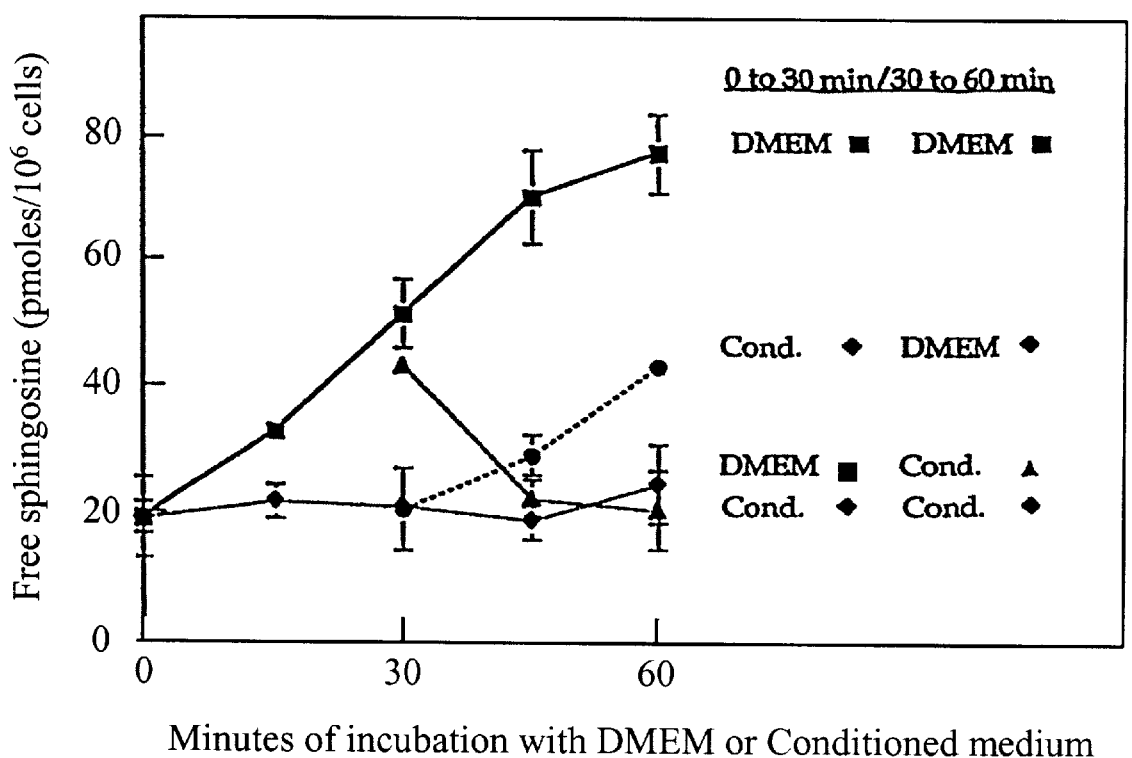
FIG. 4 is a graph showing the reversibility of the elevation in free sphingosine mass by readdition of conditioned culture medium. J774 cells were cultured for 3 days, then the conditioned culture medium was removed and replaced with fresh medium (without FBS) for various times. Results are the mean±range (pmol/10$^6$ cells) from duplicate samples of a representative experiment.

To confirm that the change from old to new culture medium removes suppressive factors, either new or "conditioned" medium was added to the cells and sphingosine measured after varying times (FIG. 4). Conditioned medium completely suppressed the burst (FIG. 3, diamonds), even if the sphingosine burst was activated by new medium (FIG. 3, squares followed by triangles). The suppressive effect of conditioned medium was also reversible (FIG. 3, squares and diamonds followed by circles). These findings confirm that conditioned medium contains factors that suppress the sphingosine "burst".

Appearance of Suppressive Factor(s) in Conditioned Medium

Figure 5:
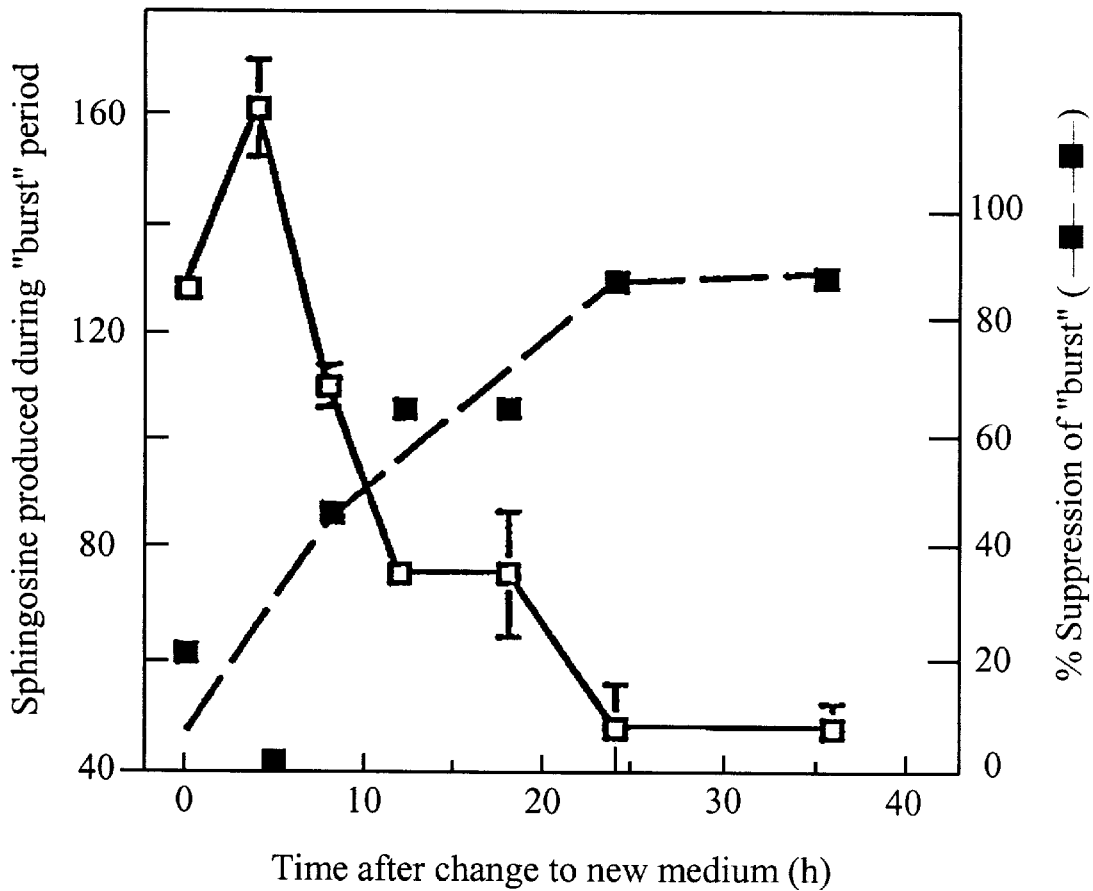
FIG. 5 is a graph showing the appearance of suppressive factors over time of culturing J774 cells in new medium. J774 cells were changed to new medium (DMEM with FBS), and at the shown time points the medium was collected and stored in sealed tubes at 4° C. until all had been collected. These conditioned media were added to new cells for measurement of the changes in sphingosine after 45 minutes (open squares), as in FIG. 3. At time zero, the cells contained 40 pmol sphingosine/10$^6$ cells. Shown are the mean+SD from triplicate dishes used for the assay. The closed squares reflect the percent suppression at each time point as compared to the highest "burst" (160 pmol/10$^6$ cells).

If J774 cells produce such factors, the amounts in conditioned medium should be time-dependent. To demonstrate this, medium was collected from cells after various intervals, then added to new cells to determine whether there was an effect on the sphingosine "burst". Shown in FIG. 5 are the amounts of sphingosine after 45 minutes of incubation of the cells with these media. New medium and media that were conditioned for greater than 8 hours allow a robust sphingosine burst, and some increase in sphingosine was seen with media conditioned for up to 18 hours. Depending on the selection of the "maximum" increase in sphingosine (i.e., at time zero or the somewhat higher amount at 4 hours) (the latter is shown in the dashed line in FIG. 5), the half time for 50% suppression was 8 to 12 hours, respectively.

Identification of $NH_4^+$ as a Suppressive Factor in Conditioned Medium

Figure 6A:
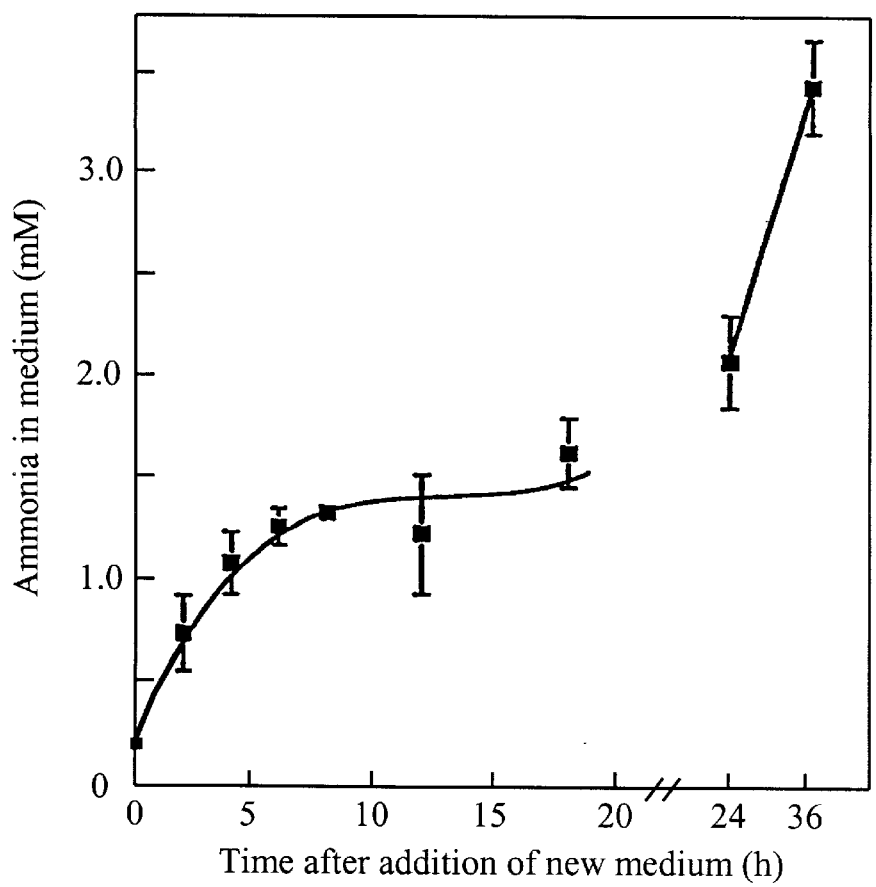
FIG. 6A is a graph showing the concentrations of ammonium ion in J774 medium over time of culture.
Figure 6B:
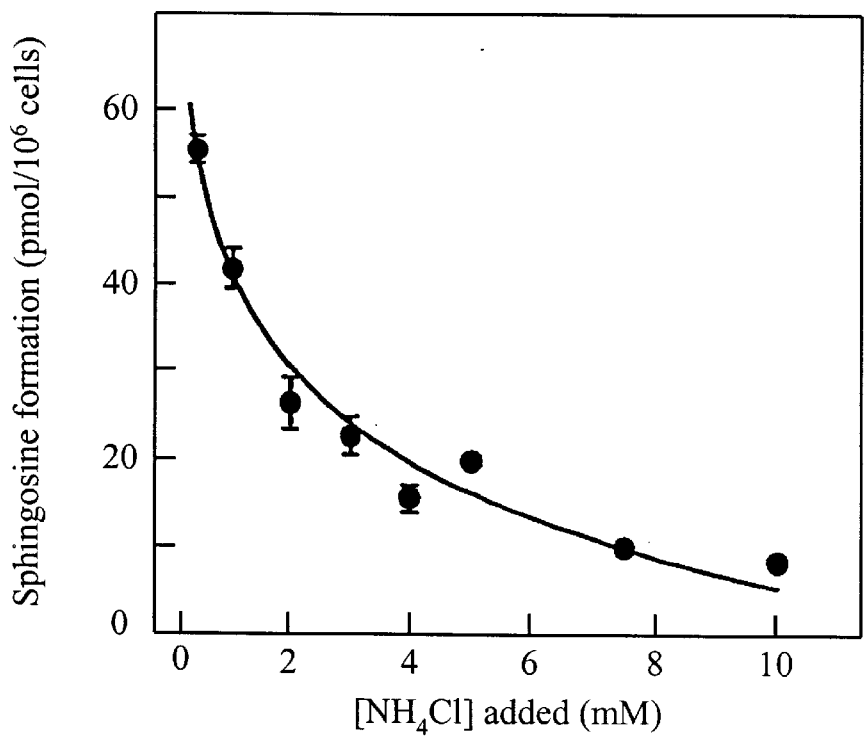
FIG. 6B is a graph showing the suppression of the sphingosine burst by exogenously added NH$_4$Cl. After various times in new medium (as in FIG. 5), aliquots were removed and stored in sealed containers at 4° C. until analysis of the ammonia concentration (panel A). For comparison, the effects of varying concentrations of NH$_4$Cl on the sphingosine burst (after 45 minutes of incubation) were measured as in FIG. 3 (lower panel). For ease in visualizing the extent of inhibition, only the increases in sphingosine during the burst are shown (i.e., the sphingosine at t0 min has been subtracted from the amount at t45 min). The results are given as the mean±SD for triplicate analyses.
Figure 7:
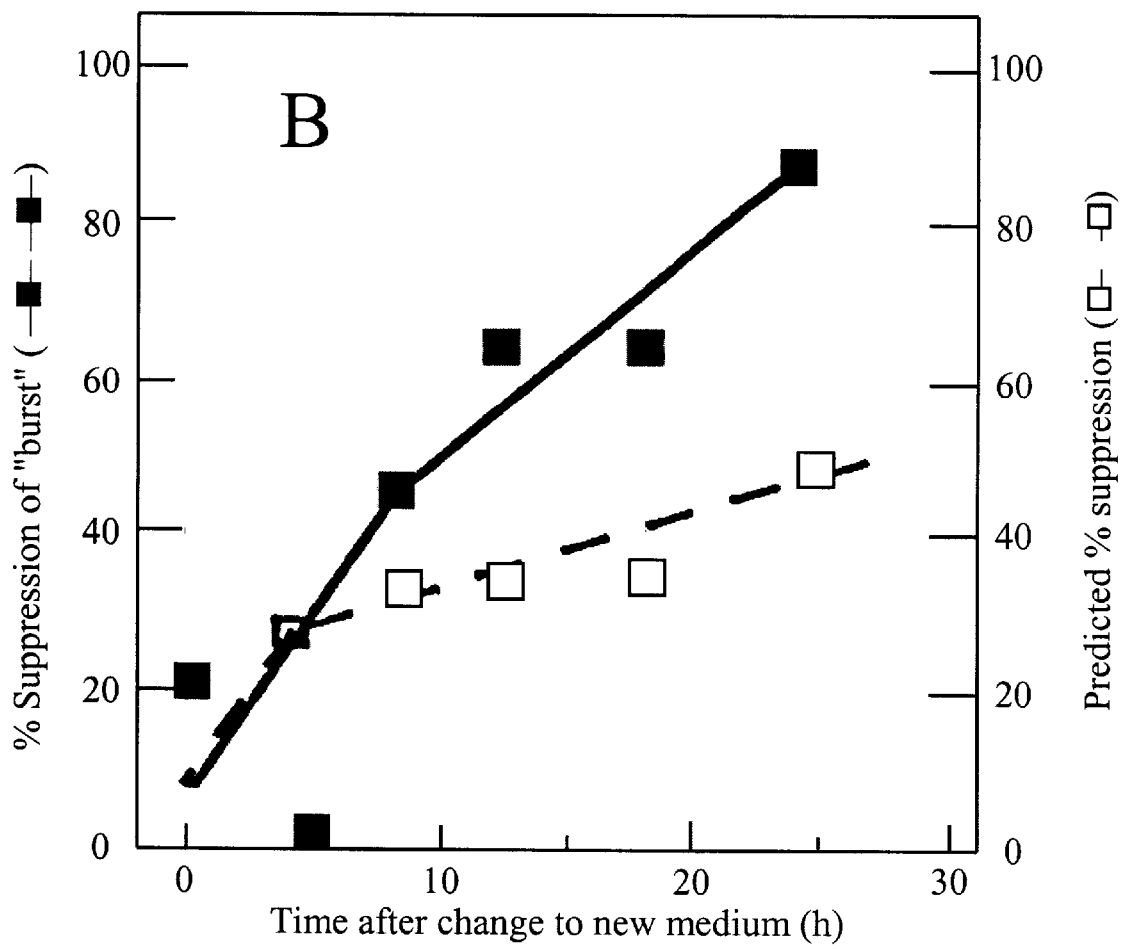
FIG. 7 is a graph showing a comparison of the time-course for appearance of suppression of the sphingosine burst by conditioned medium and the percent suppression predicted by the ammonia concentration of the conditioned medium. The predicted suppression of sphingosine burst by the concentrations of ammonia in the dishes at different time points (from FIGS. 6A and B) is shown by the dashed line (open squares) and the observed suppression (from FIG. 5) is shown by the solid line (closed squares).

One component of the conditioned culture media, shown to suppress the sphingosine burst of J774 cells, was $NH_4^+$, apparently due to neutralization of acidic compartments in the cells. Ammonium ion is produced by amino acid catabolism and non-enzymatic deamidation of glutamine, hence, $NH_4^+$ can be measured in culture medium after varying intervals (FIG. 6A). Over the first 4 to 8 hours, the $NH_4^+$ concentration rose to about 1.4 mM, and continued to increase to >3 mM at 36 hours. The results in FIGS. 6A and B were used to calculate the expected suppression of the sphingosine burst by ammonia, and these estimates (FIG. 7 dashed line) and the actual suppression can be compared (FIG. 7). At most time points, the ammonia concentration of the conditioned medium could account for greater than 50% of the suppression of the sphingosine burst.

Purification of Suppressive Factors from Conditioned Medium

The medium was then fractionated to isolate factor suppression factors other than $NH_4^+$. The first analyses determined whether the factors were of high or low molecular weight. Conditioned medium was dialyzed against water using membranes with a 6,000 to 8,000 molecular weight cut-off. The dialysate was lyophilized and re-dissolved to the volume of the original conditioned medium. Assay of the same volumes of the retained and low-molecular weight fractions found no inhibition by the former and 97% suppression by the latter. Similar results were obtained using dialysis membranes with a 3500 molecular weight cut-off. Thus, as a first step for purification of the factors from conditioned medium, the medium was passed through a Diaflo™ hollow fiber filtration system with a 2,000–3,000 dalton cut-off. When the ultra-filtrate was analyzed, it had 80 to 90% of the potency of the original condition medium for suppression of the sphingosine burst (data not shown).

Figures 8A, 8B:
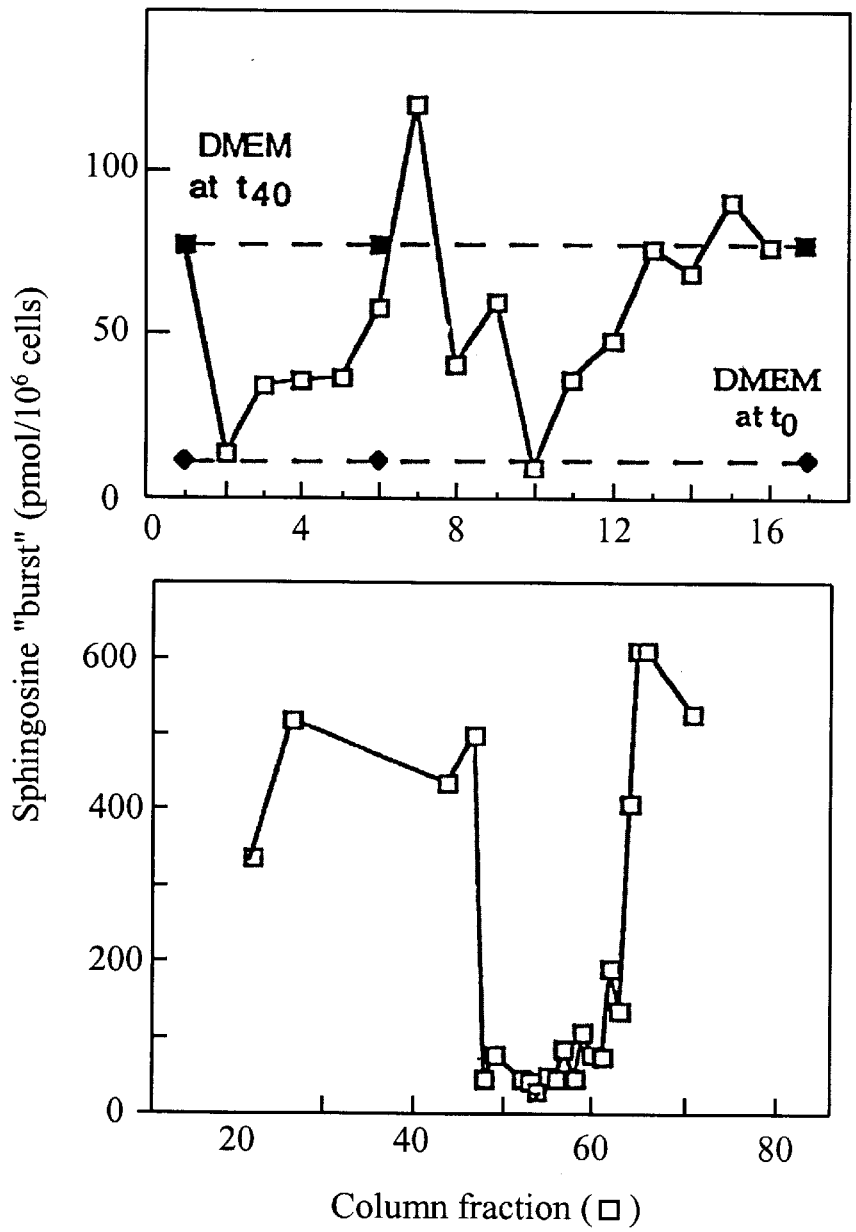
FIG. 8A is a graph showing the elution of suppressive "factors" upon cation exchange chromatography.
FIG. 8B is a graph showing the elution of suppressive "factors" upon size exclusion chromatography. Low molecular weight species were obtained from conditioned medium by ultrafiltration using membranes with a 2000 to 3000 dalton cut-off, then applied to a Bio-Rex 70 column (6×15 cm) followed by elution with deionized water containing increasing concentrations of NaCl (upper panel, open circles). Shown in A is the elution profile, with suppressive activity reflected as a decrease in the amount of sphingosine that was formed by J774 cells incubated with aliquots of each fraction as described in the text. For comparison, the magnitude of the burst in DMEM alone (expressed as 100%) is shown by the upper dashed line (40 min in DMEM alone) versus the lower dashed line, the amount of sphingosine in cells at time zero (which was also the same as the amount in cells incubated with unfractionated conditioned medium).

The ultrafiltrate was applied to cation and anion exchange columns but the suppressive activities did not bind to anion exchange columns (data not shown). Shown in FIG. 8A is the elution profile using the cation exchange resin Bio-Rex 70™ with elution by water and 0, 0.1, and 0.5 M NaCl. The column fractions were assayed by adding aliquots to DMEM and incubating the new medium with J774 cells, therefore, fractions that contained suppressive factors showed little or no increase in sphingosine after 45 minutes versus the zero time point. There was some suppressive activity in the column flow through and initial washes, but the majority remained on the column and was eluted by 0.5 M NaCl.

The 0.5 molar NaCl eluate was lyophilized and applied to a BIO-GEL P2™ gel filtration column. The suppressive factor eluted from this gel filtration column as a broad band of activity which, when compared to the volumes of elution of several standards, suggests that the molecular weights for Fractions III and IV were about 240 and 130 daltons, respectively (FIG. 8B) (similar results were obtained using SEPHADEX G10™ columns, data not shown). Four regions of the eluate (I to IV in FIG. 8B) were examined by silica and cellulose thin layer chromatography, and fraction III was found to be the only eluate that contained a single species (see below in Example 2 for Rf). Therefore, the compound was characterized further. The compounds in the other fractions were also ninhydrin positive, but did not yield the blue-grey product with ortho-phalthaldehyde that was obtained with III (see below).

Figure 9:
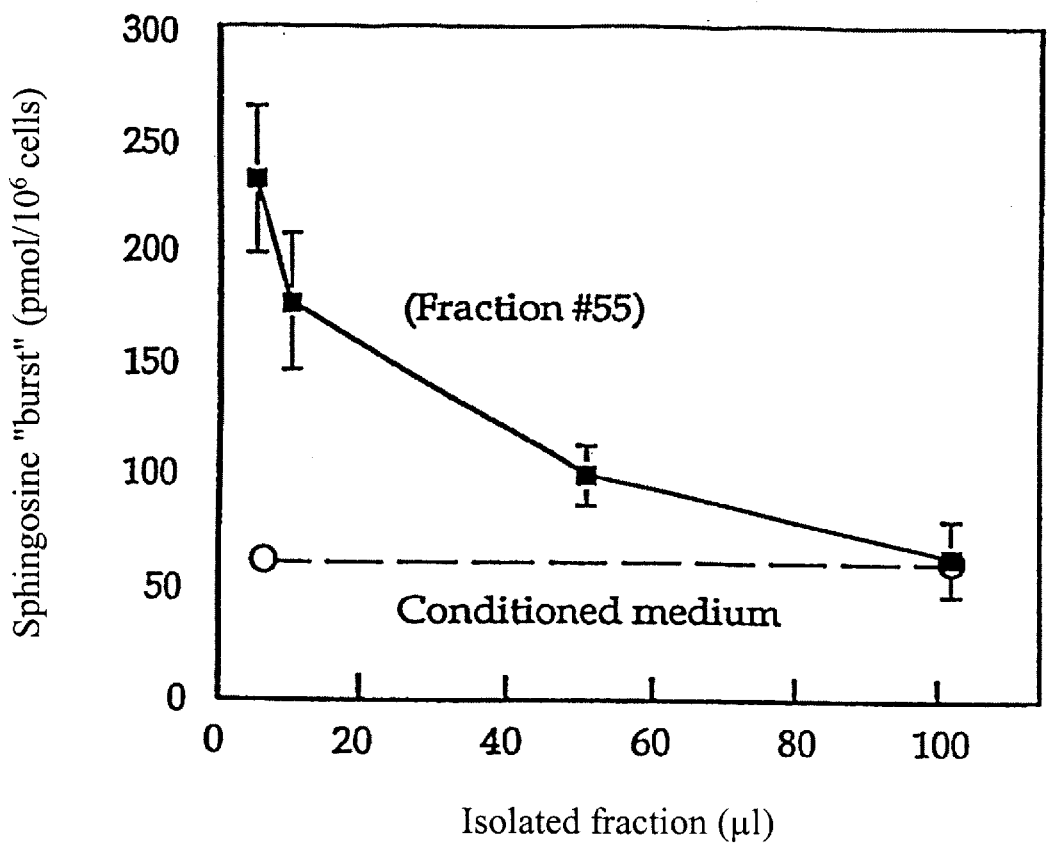
FIG. 9 is a graph showing the concentration dependence of the suppression of the sphingosine burst by a factor purified from the conditioned medium of J774A.1 cells. The shown volumes of the purified factor (fraction III from FIG. 8B) were added with DMEM to J774 cells to initiate the sphingosine burst. The amount of sphingosine in cells that are given three-day conditioned medium, instead of new medium, is shown by the open circles and the lower dashed line. The results are given as mean±SD of triplicate analyses.

The organic amine content of fraction III was estimated by reaction with TNBS (2,4,6 trinitrobenzene sulfonic acid) (in accordance with the method described by Fields, R. (1972) *Meth. Enzymol.* 25, 464–468). Although this was only an approximation, it suggests that the amine concentration was about 200 mM. Titration of the sphingosine burst with the purified fraction III (FIG. 8B) revealed 50% suppression of the burst with 30 ml, or an apparent concentration of 1 to 3 mM (FIG. 9). Based on a volume to volume comparison of the amount of fraction III that was needed to suppress the sphingosine burst comparable to that of conditioned medium, the fraction is greater than 200-fold more concentrated than conditioned medium. Since the purification produces 3 ml of this fraction from 3,000 ml of conditioned culture medium, the yield for the procedure appears to be 22%.

EXAMPLE 2

Characteristics of the Purified Suppressive Factor

On both silica and cellulose thin layer chromatography plates, the suppressive factor reacted with ninhydrin to give an orange compound that was fluorescent under long wave length ultraviolet light, and with ortho-phthalaldehyde gave a blue gray spot. The Rf (versus the solvent front) on cellulose plates was 0.40 (for comparison, the Rf for tryptamine is 0.7, for tryptophan, 0.5, for glucosamine, 0.24, and for lysine, 0.1); on silica the Rf was 0.56 (plus some color at the origin) (the Rf for tryptamine is 0.12, for tryptophan, 0.5, for glucosamine, 0.21, and lysine and arginine are slightly above the origin). In addition, the isolated suppressive factor was Ehrlich reagent negative and, therefore, not an indole amine, pyrrole, aromatic amine, sulfonamide, urea, or allantoin; did not react with vanillin and therefore, was not proline, a polyhydric sugar, an aldopentose, an aldohexose, inositol or ornithine; was not visualizable with iodine vapor, which makes it unlikely that it is a lipid, a catecholamine, a sugar mercaptal, an alcohol, a glycoside, or an N-acylamino sugar (a close running, $I_2$-positive contaminant was, however, found in some impure extracts). For further confirmation that the amine was not a standard amino acid, it was submitted to the Emory Microchemical Center (Atlanta, Ga.) for amino acid analysis, which failed to account for more than 2% of the total amine content as known amino acids. Hence, these are minor contaminants but not the major species. The $NH_4^+$ concentration was also low (0 to 0.04 mM).

EXAMPLE 3

Structural Determination of the Novel Suppressive Factor

The chemical identity of the compound in fraction III was elucidated by a combination of methods and the structure that was consistent with all of the analytical data was 2,6-bis-(w-aminobutyl)-3,5-diimino-piperazine.

High resolution mass spectrometry (FAB-ion mode) gave an m/z for the factor of 255.2295, which provides the molecular composition of $C_{12}H_{28}N_6$. Electrospray ionization mass spectrometry gives a $M^+H^+$ ion at m/z 257, which is also consistent with a protonated species of this composition.

The $^1$H-NMR spectrum in $D_2O$ revealed five distinct signals integrating in a 1:2:2:2:2 ratio, while the $^{13}$C-NMR spectrum showed six absorptions with five clustered in the aliphatic region below 55 ppm and one signal at 174.6 ppm. An attached proton test established that the $^{13}$C spectrum was comprised of four methylenes, one methine, and one non-protonated carbon signal. Since the mass spectrum required twelve carbons, these data confirm that the compound is comprised of two identical elements, as shown in the structure 2,6-bis-(w-aminobutyl)-3,5-diimino-piperazine provided above.

The two sites of unsaturation required by the molecular formula were assigned to the amide groups (dc 174.6) based on a strong absorption at 1586 cm$^{-1}$ in the IR spectrum. The remaining mass units were accommodated by two terminal primary amines. The presence of amine and amidine groups was supported by strong absorptions at 3446 cm$^{-1}$ in the IR spectrum, characteristic of exchangeable hydrogens on nitrogen.

COSY and HMQC analyses confirm that the methine carbon ($\delta$54.2, C-6 in FIG. 2) correspond to the $^1$H-NMR signal at $\delta$3.61 and is connected to a chain of methylenes as follows: C-7 and C-7': $^1$H-NMR, $\delta$1.74 (4H); $^{13}$C-NMR, 29.9: C-8 and C-8': $^1$H-NMR, $\delta$1.38 (4H); $^{13}$C-NMR, 21.5; C-9 and C-9': $^1$H-NMR, $\delta$1.58 (4H); $^{13}$C-NMR, 26.4: and, C-10 and C-10': $^1$H-NMR, §$\delta$2.87 (4H): $^{13}$C-NMR, 39.2. Analysis of the decoupled one-dimensional spectra also revealed that the aliphatic signal furthest downfield ($\delta$3.76 t) assigned to C-2 and C-6 in the parent structure is coupled to C-7 methylene protons ($\delta$1.74) which in turn is coupled to the C-8 methylene protons ($\delta$1.38). The methylene protons assigned to C-10 and C-10' ($\alpha$ to the amine) are second furthest downfield ($\delta$2.87, t) and are coupled only to the C-9 and C-9' protons ($\delta$1.58). The C-2 and C-6 protons show, as expected for the structure in the figure, coupling to C-7 and C-7' methylene protons. The splitting and couplings are consistent with a straight chain of methylene units with the terminal methylene unit ($\delta$2.87, C-6) connected to a primary amino group.

There was no clear evidence for coupling of the two methylene protons to each other, which distinguished 2,6-bis(w-aminobutyl)-3,5-diiminopiperazine as the most likely structure versus 1,10-diamino-5,6-diamidinodecane, which is otherwise consistent with all of these analytical data. The isomer 2,5-bis(w-aminobutyl)-3,5-diiminopiperazine might also fit the analytical data but, according to energy minimization calculations, would be most stable with the double bonds in the pyrazine ring and is not as easy to rationalize by a simple biosynthetic pathway.

All of the patents, publications and other references mentioned herein are hereby incorporated by reference.

Modifications and variations of the present methods and compositions will be obvious to those skilled in the art from the foregoing detailed description. Such modifications and variations are intended to come within the scope of the appended claims.

We claim:

1. A composition comprising a diimino compound that inhibits, in a cationic form, sphingolipid metabolism; wherein the diimino compound has a molecular weight between 112 and 3000 Daltons; and wherein the diimino compound has the following structural formula:

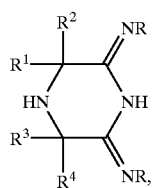

wherein
R is independently H, alkyl, aryl, heteroaryl, —C(O)R, —C(NR)OR, —C(O)NR$_2$, —C(NR)NR$_2$, —C(NR)SR or —C(S)NR$_2$;

$R^1$, $R^2$, $R^3$ and $R^4$ are independently H, R, $(CH_2)_n$OR, $(CH_2)_n$NR$_2$, CH$_2$O(CH$_2$)$_n$OR, or CH$_2$O(CH$_2$)$_n$NR$_2$ where n=1 to 6; and wherein H$^+$ or other cationic species can form an association between any electronegative atom of the diimino compound; and wherein the term alkyl refers to a saturated straight, branched, or cyclic, primary, secondary, or tertiary hydrocarbon, typically of $C_1$ to $C_{18}$ and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl and 2,3-dimethylbutyl; and wherein the alkyl group can be optionally substituted with one or more moieties selected from halo, hydroxyl, carboxylic acid or ester, amino, alkylamino, arylamino, alkoxy, aryloxy, nitro, cyano, sulfonic acid, sulfate, phosphonic acid, phosphate, or phosphonate, either unprotected or protected; and wherein the term aryl refers to phenyl, biphenyl, or naphthyl, and wherein the aryl group can be optionally substituted with one or more moieties selected from the group consisting of halo, hydroxyl, amino, alkylamino, arylamino, alkoxy, aryloxy, nitro, cyano, sulfonic acid, sulfate, phosphonic acid, phosphate or phosphonate, either unprotected, or protected; and wherein the aryl group can be substituted with an alkyl group as described above, and/or a halo group; and wherein the term heteroaryl refers to a cyclic moiety that includes at least one sulfur, oxygen, or nitrogen in the ring, including, but not limited to, furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isoxazolyl, pyrrolyl, quinazolinyl, pyridazinyl, pyrazinyl, cinnolinyl, phthalazinyl, quinoxalinyl, xanthinyl, hypoxanthinyl, and pteridinyl; and wherein the oxygen and nitrogen groups on the heteroaryl group can be protected or unprotected; and wherein the heteroaryl can be substituted with an alkyl group as described above; and, wherein the term "protected" refers to a group that is added to an oxygen, nitrogen, or phosphorus atom to prevent its further reaction, or for other purposes; and wherein suitable protecting groups include, but are not limited to, trimethylsilyl, triethylsilyl, dimethylhexylsilyl, t-butyldimethylsilyl, t-butyldiphenylsilyl and triisopropylsilyl.

2. A composition of claim 1, wherein the diimino compound, in a cationic form, inhibits sphingosine burst.

3. The composition of claim 1, wherein the diimino compound has a molecular weight between 130 and 300 Daltons.

4. The composition of claim 2, wherein the diimino compound is 2,6-bis-(ω-aminopropyl)-3,5-diimino-piperazine, having the following structural formula:

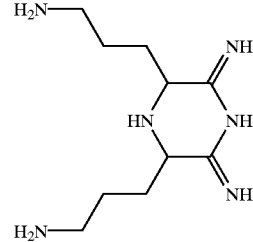

5. The composition of claim 2, wherein the diimino compound is 2,6-bis-(ω-aminobutyl)-3,5-diimino-piperazine, having the following structural formula:

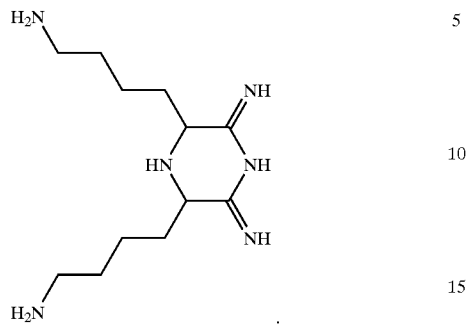

6. The composition of claim 5, wherein the diimino compound is isolated from a biological sample.

7. A method of inhibiting sphingolipid metabolism associated with a cell signaling pathway disease or disorder, comprising administering to a patient having the disease or disorder, a therapeutic dose of a composition comprising a diimino compound in a cationic form; wherein the diimino compound has a molecular weight between 112 and 3000 Daltons; and wherein the diimino compound has the following structural formula:

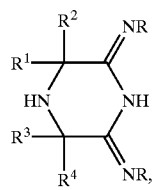

wherein
R is independently H, alkyl, aryl, heteroaryl, —C(O)R, —C(NR)OR, —C(O)NR$_2$, —C(NR)NR$_2$, —C(NR)SR or —C(S)NR$_2$;

$R^1$, $R^2$, $R^3$ and $R^4$ are independently H, R, (CH$_2$)$_n$OR, (CH$_2$)$_n$NR$_2$, CH$_2$O(CH$_2$)$_n$OR, or CH$_2$O(CH$_2$)$_n$NR$_2$ where n=1 to 6; and wherein H$^+$ or other cationic species can form an association between any electronegative atom of the diimino compound; and wherein the term alkyl refers to a saturated straight, branched, or cyclic, primary, secondary, or tertiary hydrocarbon, typically of C$_1$ to C$_{18}$ and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl and 2,3-dimethylbutyl; and wherein the alkyl group can be optionally substituted with one or more moieties selected from halo, hydroxyl, carboxylic acid or ester, amino, alkylamino, arylamino, alkoxy, aryloxy, vitro, cyano, sulfonic acid, sulfate, phosphonic acid, phosphate, or phosphonate, either unprotected or protected; and wherein the term aryl refers to phenyl, biphenyl, or naphthyl, and wherein the aryl group can be optionally substituted with one or more moieties selected from the group consisting of halo, hydroxyl, amino, alkylamino, arylamino, alkoxy, aryloxy, nitro, cyano, sulfonic acid, sulfate, phosphonic acid, phosphate or phosphonate, either unprotected, or protected; and wherein the aryl group can be substituted with an alkyl group as described above, and/or a halo group; and wherein the term heteroaryl refers to a cyclic moiety that includes at least one sulfur, oxygen, or nitrogen in the ring, including, but not limited to, furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isoxazolyl, pyrrolyl, quinazolinyl, pyridazinyl, pyrazinyl, cinnolinyl, phthalazinyl, quinoxalinyl, xanthinyl, hypoxanthinyl, and pteridinyl; and wherein the oxygen and nitrogen groups on the heteroaryl group can be protected or unprotected; and wherein the heteroaryl can be substituted with an alkyl group as described above; and wherein the term "protected" refers to a group that is added to an oxygen, nitrogen, or phosphorus atom to prevent its further reaction, or for other purposes; and wherein suitable protecting groups include, but are not limited to, trimethylsilyl, triethylsilyl, dimethylhexylsilyl, t-butyldimethylsilyl, t-butyldiphenylsilyl and triisopropylsilyl.

8. The method of claim 7, wherein the diimino compound, in a cationic form, inhibits sphingosine burst.

9. The method of claim 8, wherein the diimino compound is 2,6-bis-(ω-aminopropyl)-3,5-diimino-piperazine, having the following structural formula:

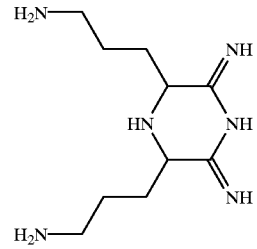

10. The method of claim 8, wherein the diimino compound is 2,6-bis-(ω-aminobutyl)-3,5-diimino-piperazine, having the following structural formula:

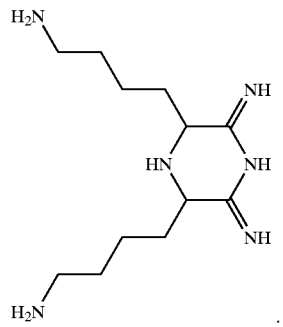

11. The method of claim 8, wherein the cell signaling pathway disease or disorder is selected from the group consisting of cancer, heart attack, stroke, and inflammatory disease.

* * * * *